United States Patent [19]
O'Donnell et al.

[11] Patent Number: 5,921,931
[45] Date of Patent: Jul. 13, 1999

[54] METHOD AND APPARATUS FOR CREATING A COLOR BLOOD FLOW IMAGE BASED UPON ULTRASONIC ECHO SIGNALS RECEIVED BY AN INTRAVASCULAR ULTRASOUND IMAGING PROBE

[75] Inventors: Matthew O'Donnell, Ann Arbor, Mich.; Michael J. Eberle, Fair Oaks, Calif.; Douglas N. Stephens, Davis, Calif.; Gerald Litzza; Randy Ziegenbein, both of Sacramento, Calif.; David Bleam, Orangevale, Calif.; Ching-Chen Wu, Citrus Heights, Calif.

[73] Assignee: EndoSonics Corporation, Rancho Cordova, Calif.

[21] Appl. No.: 08/827,724

[22] Filed: Apr. 8, 1997

[51] Int. Cl.⁶ ..................................................... A61B 8/00
[52] U.S. Cl. .......................... 600/441; 600/455; 600/463; 382/162; 382/261
[58] Field of Search ................................... 600/437, 441, 600/442, 443, 447, 453–455, 463; 128/916; 382/162, 261–265, 270

[56] References Cited

U.S. PATENT DOCUMENTS 5,442,462 8/1995 Guissin ................................... 358/463
5,476,096 12/1995 Olstad et al. ........................... 600/443
5,494,037 2/1996 Banjanin et al. ....................... 600/455
5,515,852 5/1996 Karp et al. ......................... 600/455 X
5,544,658 8/1996 Kim et al. .............................. 600/455
5,609,155 3/1997 Guracar ................................. 600/453
5,662,115 9/1997 Torp et al. ............................. 600/455

FOREIGN PATENT DOCUMENTS

0871043 A2 10/1998 European Pat. Off. .

OTHER PUBLICATIONS

European Search Report for EPA EP 0 871 043 A3, dated Sep. 9, 1998, published Oct. 28, 1998.

*Primary Examiner*—Francis J. Jaworski
*Attorney, Agent, or Firm*—Leydig, Voit & Mayer, Ltd.

[57] ABSTRACT

A blood flow detection and imaging method and system is described for displaying images in accordance with signals transmitted from an intravascular ultrasound transducer probe. The image processor includes means for independently designating persistence factors for smoothing calculated speed and power of the dynamic portion of a field of view within a vasculature. Furthermore, the designation of a particular image point within a field of view as a dynamic image point (such as a blood flow region) as opposed to a static image point (such as a tissue region) is determined by averaging signal values for image points proximate to an image point of interest over both time and space.

40 Claims, 8 Drawing Sheets

METHOD AND APPARATUS FOR CREATING A COLOR BLOOD FLOW IMAGE BASED UPON ULTRASONIC ECHO SIGNALS RECEIVED BY AN INTRAVASCULAR ULTRASOUND IMAGING PROBE

INCORPORATION BY REFERENCE

The applicants hereby expressly incorporate by reference in their entirety the description of an "Apparatus and Method for Imaging Small Cavities" described in Proudian et al. U.S. Pat. No. 4,917,097, the description of a "Dilating and Imaging Apparatus" described in Eberle et al. U.S. Pat. No. 5,167,233, the description of an "Ultrasound Catheter" described in Eberle et al. U.S. Pat. No. 5,368,037, the description of an "Apparatus And Method For Detecting Blood Flow In Intravascular Ultrasonic Imaging" in O'Donnell et al. U.S. Pat. No. 5,453,575, and the description of a "High Resolution Intravascular Ultrasound Transducer Having a Flexible Substrate" in Eberle et al. U.S. Ser. No. 08/712,576 filed on Sep. 13, 1996 which is a continuation of U.S. Ser. No. 08/578,226 filed on Dec. 26, 1995 and now abandoned, and the description of a "A High Resolution Intravascular Ultrasound Transducer Assembly Having a Flexible Substrate and Method For Manufacture Thereof" in Eberle et al. U.S. Ser. No. 08/780,437 filed on Jan. 8, 1997 and now U.S. Pat. No. 5,857,974.

FIELD OF THE INVENTION

This invention relates generally to imaging systems, and more particularly to a system for creating images containing both static and dynamic regions, such as a view of a blood vessel comprising flowing blood and relatively stationary tissue. Furthermore, the present invention is particularly directed to displaying an image rendered by the ultrasound imaging system of the dynamic portions of the field of view in vatrious ones of multiple colors associated with varying degrees of dynamic behavior, and wherein the colorizedt dynamic image is superimposed upon an image of relatively static features represented in gray scale format.

BACKGROUND OF THE INVENTION

In the United States and many other countries, heart disease is the leading cause of death and disability. One particular kind of heart disease is atherosclerosis, which involves the degeneration of the walls and lumen of the artery walls throughout the body. Scientific studies have demonstrated the thickening of the arterial wall and eventual encroachment, of the tissue into the lumen as fatty material is built up. This material is known as "plaque." As the plaque builds up and the lumen narrows, blood flow is restricted. If the artery narrows too much, or if a blood clot forms at an injured plaque site (lesion), flow is severely reduced, or cut off and consequently the muscle that it supports may be injured or die due to a lack of oxygen. Atherosclerosis can occur throughout the human body, but it is most life threatening when it involves the coronary arteries which supply oxygen to the heart. If blood flow to heart muscle is significantly reduced or cut off, a myocarcial infarction or "heart attack" often occurs. If not treated immediately a heart attack frequently leads to death.

The medical profession relies upon a wide variety of tools to treat coronary disease, ranging from drugs to open heart "bypass" surgery. Often, a 9 lesion can be diagnosed and treated with minimal intervention using catheter-based tools threaded into the coronary arteries via the femoral artery in the groin. For example, one treatment for lesions is a procedure known as percutaneous transluminal coronary angioplasty (PTCA) whereby a catheter with an expandable balloon at its tip is threaded into the lesion and inflated. The underlying lesion is re-shaped, and hopefully, the lumen diameter is increased to restore blood flow.

The practiced method for guiding a catheter during procedures such as PTCA is real time X-ray images. With this method, a radiopaque dye is injected into the coronary tree to provide a map of blood flow. This technique helps a physician to identify sites where blood flow is restricted. After identifying these sites, therapeutic devices are positioned using a live X-ray image. However, the X-ray image does not give information about the morphology, i.e., form and structure, of the artery.

In the last 10 years, cardiologists have adopted a new technique to obtain information about the coronary vessel and to help view the effects of therapy on the form and structure of the vessel and not just the blood flow. This technique, known as Intracoronary or Intravascular Ultrasound (ICUS/IVUS) employs miniaturized transducers on the tip of the catheter which provide electronic signals to an external imaging system in order to produce a two or three-dimensional image of the lumen, the arterial tissue, and tissue surrounding the artery. These images are generated in substantially real time and have a high degree of resolution. As an improvement over X-ray imaging, the transducers facilitate the construction of images of the exact site where the transducers are placed. within the vessel.

Several ICUS/IVUS devices are now commercially available for sale in the United States and. other countries. These devices include a transducer probe assembly having either a solid state transducer array or a rotating crystal. The physician is most interested in identifying the size and shape of the lumen, and any flaps or tears in the plaque. Commercially available systems produce detailed images of these relatively static features due to the relatively high frequency of ultrasound they employ. Image signals are typically transmitted at frequencies between 10 and 40 MHz.

As previously explained in O'Donnell et al. U.S. Pat. No. 5,453,575, there is a common problem associated with these devices operating at such high frequencies. As the frequency of the ultrasound is raised, the backscatter from blood increases as the fourth power of the frequency. At frequencies of around 30 MHz, the amplitude of the backscatter from blood approaches the amplitude of the backscatter and reflections from arterial tissue. Because of this phenomenon, the image of the lumen is filled with blood echoes, and it is often difficult to delineate blood from surrounding tissue. Therefore, the physician has trouble defining the lumen.

The problem of blood echoes has been addressed in a number of different manners imaging dynamic regions in a field of view. An example of such a system and method is provided in O'Donnell et al. U.S. Pat. No. 5,453,575 wherein a "dynamic" image is generated and thereafter superimposed upon a second image representing relatively static features of a field of view in a vasculature.

While the known imaging systems and methods helped distinguish dynamic and static features in a field of view during intravascular imaging, certain shortcomings were encountered. First, the known intravascular blood flow imaging systems and methods tend to present slow moving tissue as a dynamic region which cannot easily be distinguished from regions of moving blood. Further, present ultrasound vascular imaging systems tend to present an unstable image wherein dynamic portions of the image change drastically from displayed frame-to-frame thereby creating distracting "flashing" displays. In other words, the color bits for a large percentage of pixels on the screen toggle between on and off states when a display is refreshed with new image data. The color assigned to particular pixels exhibits similar instabilities.

SUMMARY OF THE INVENTION

It is a general object of the present invention to provide an improved blood flow image during intravascular imaging by means of ultrasonic imaging apparatuses.

A more particular general object of the present invention is to provide an improved method for generating an image of a field of view within a vasculature that provides a clear image of blood by distinguishing regions of blood flow from relatively static feature regions.

It is an object of the present invention to construct images of blood vessels wherein regions of blood flow are readily discernable from the vessel wall and surrounding tissue.

It is a more particular object of the present invention to provide improved means for distinguishing blood flow regions from slow moving tissue regions during intravascular imaging.

It is yet another object of the invention to provide an improved method of generating a composite image of a field of view based upon static and dynamic image data.

It is a more specific object of the invention to eliminate "flashing" of pixels between color and non-color states.

It is another object of the present invention to provide an apparatus that enables a viewer of an ICUS/IVUS image to easily differentiate between an image of the blood flow region in a vessel cross-section and a simultaneously displayed image of the vessel and surrounding tissue.

It is a related object of the present invention to display on a monitor the blood flow region in a blood vessel in a manner which highly contrasts the blood flow region from the vessel wall and surrounding tissue.

It is another object of the present invention to construct the aforementioned images in a manner that visually appears to approach real-time imaging.

The above and other objects are fulfilled in a method and apparatus for providing an image of a field of view including dynamic regions. More particularly in accordance with the present invention an image of a field of view is displayed based upon image data having both motion frequency and motion power components. Motion frequency is represented in the form of designated colors for image points and motion power is represented in the form of brightness levels in the color image points.

More particularly in accordance with the new imaging method and apparatus, instantaneous motion power data is generated for an imaged field of view. Instantaneous motion frequency data is also generated for the imaged field of view. The motion frequency data corresponds to the rate of change (or flow speed) of material within the individual image regions within the imaged field of view. In the case of blood flow imaging, the frequency data corresponds to the speed of blood flow for image regions within a field of view.

In accordance with an aspect of the new imaging method and apparatus, a time averaged motion power is calculated based upon an instantaneous motion power data set, a feedback motion power, and at least a first persistence factor. A time averaged motion frequency is calculated based upon an instantaneous motion frequency data set, a feedback motion frequency, and at least a second persistence factor distinct from the first persistence factor. The time averaged motion power and time averaged motion frequency are used by the image processing system to define a color image. Thereafter, an image for display on a visual display device is generated in accordance with the color image.

In accordance with another aspect of the new imaging method and apparatus, image signal states for particular image points are determined by means of space-time filtering a particular display characteristic (colorization). More particularly, image point values corresponding to a set of image points proximate to the designated image point for a current image frame and for a set of image frames generated in a period of time proximate to the current image frame, are summed to obtain a time and space averaged value for the designated image point. Next, the image processor compares the time and space averaged value to at least one threshold value to assign one of the at least two potential signal states for the designated image point. In the particular example described below, the signal state identifies whether a particular image point is to be color or gray-scale. When a final image is presented by the image processing system, a displayed image point is at least partially defined by the assigned signal state for the image point.

BRIEF DESCRIPTION OF THE DRAWINGS

The appended claims set forth the features of the present invention with particularity. The invention, together with its objects and advantages, may be best understood from the following detailed description taken in conjunction with the accompanying drawings of which:

DETAILED DESCRIPTION OF THE PREFERRED EMBODIMENT

Figure 1:
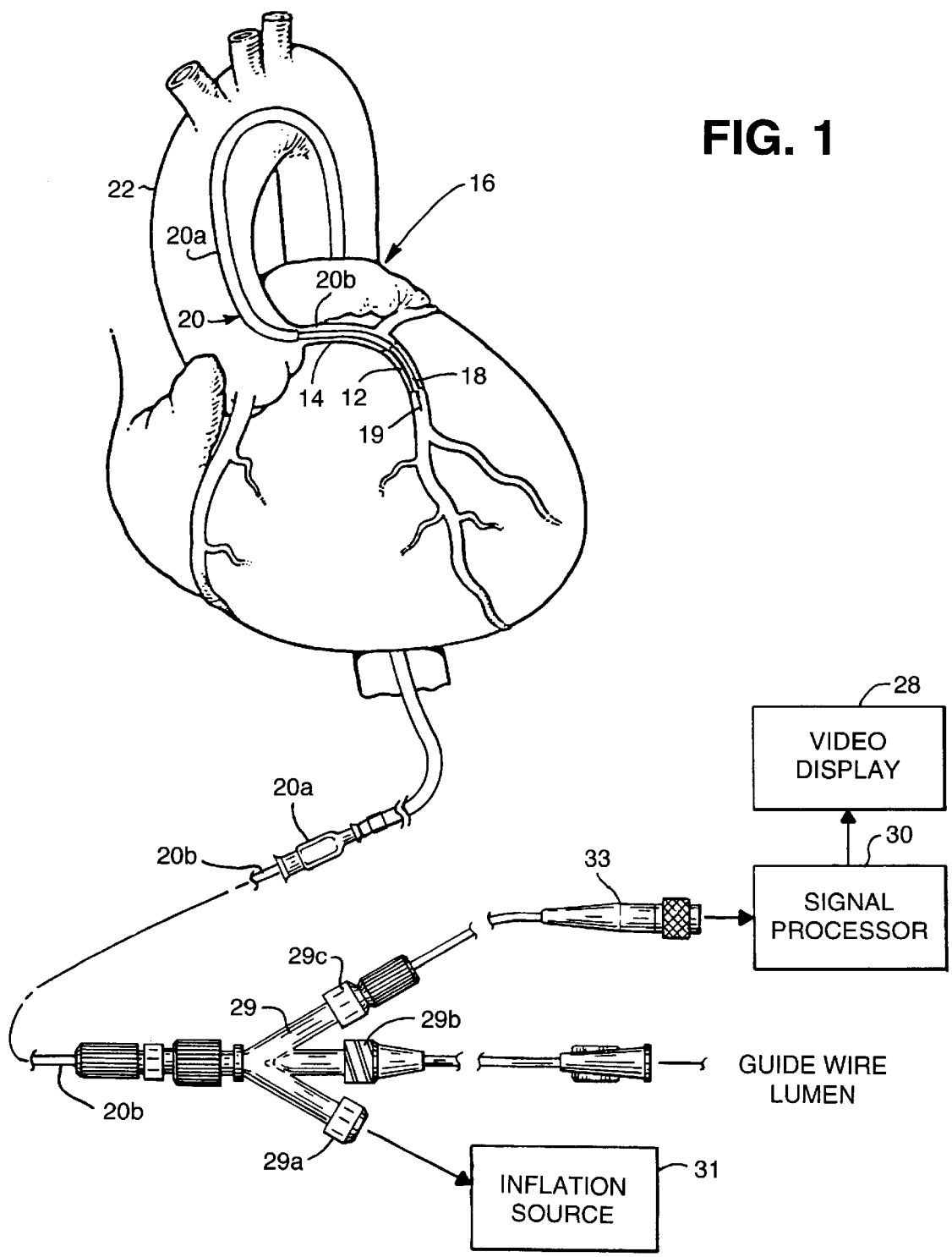
FIG. 1 is a schematic drawing of the ultrasound imaging system for incorporating the present invention and demonstrating the use of the device to image a coronary artery.
Figure 2:
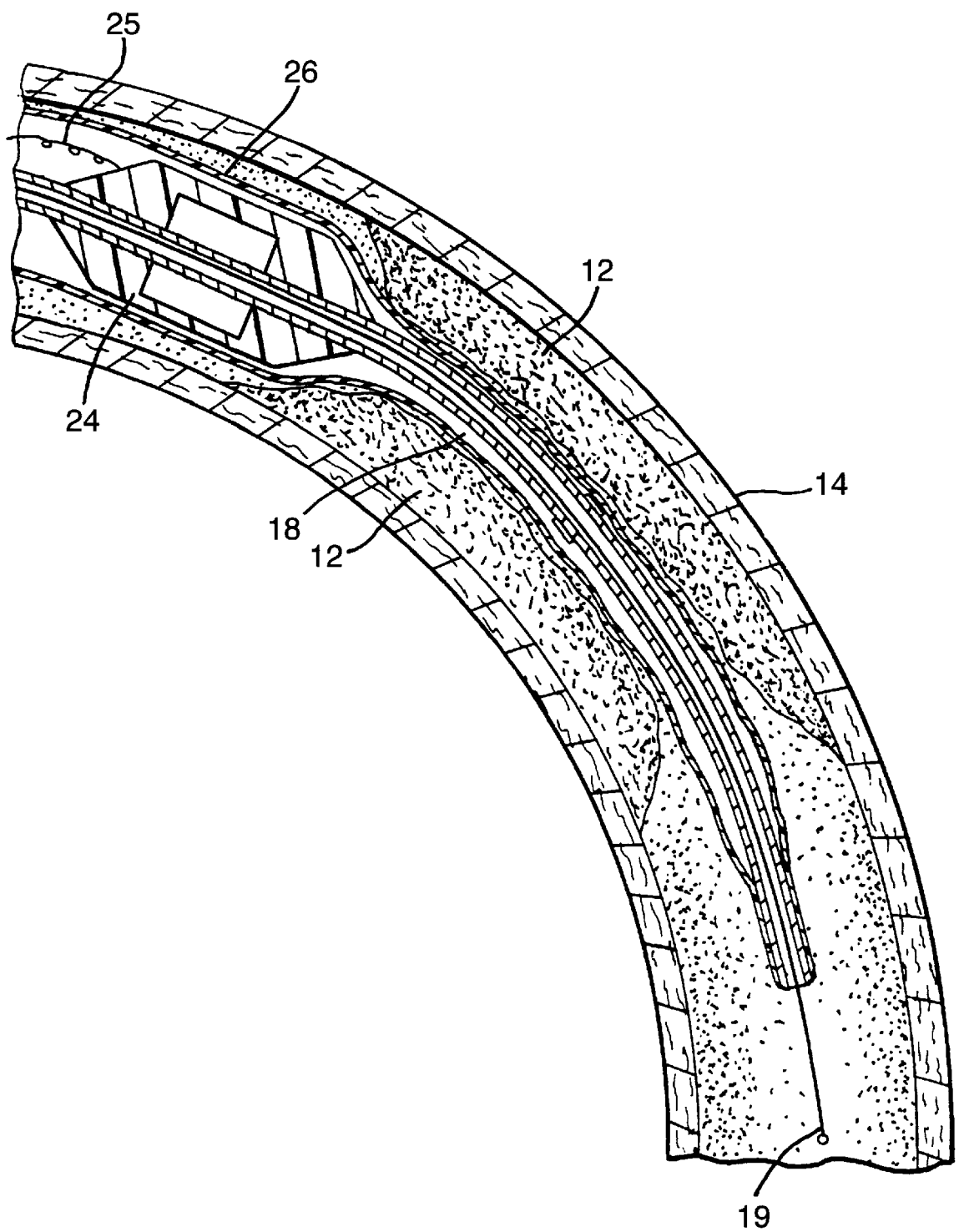
FIG. 2 is an enlarged and partially sectioned view of a portion of the coronary artery of FIG. 1 showing the probe assembly of an ultrasonic imaging device located proximate to a balloon.

Turning to the illustrated embodiment and referring to FIGS. 1–2, a buildup of fatty material or plaque 12 in a coronary artery 14 of a heart 16 may be treated in certain situations by inserting a balloon 18, in a deflated state, into the artery via a catheter assembly 20. As illustrated in FIG. 1, the catheter assembly 20 is a three-part assembly, having a guide wire 19, a guide catheter 20a for threading through the large arteries such as the aorta 22 and a smaller diameter catheter 20b that fits inside the guide catheter 20a. After a surgeon directs the guide catheter 20a and the guide wire 19 through a large artery leading to the aorta 22, the smaller catheter 20b is inserted. At the beginning of the coronary artery 14 that is partially blocked by the plaque 12, the guide wire 19 is first extended into the artery, followed by catheter 20b, which includes the balloon 18 at its tip.

Once the balloon 18 has entered the coronary artery 14, as in FIG. 2, an ultrasonic imaging device including a probe assembly 24 housed within the proximal sleeve 26 of the balloon 18 provides a surgeon with a cross-sectional view of the artery on a video display 28. The probe assembly 24 may comprise separate carrier and backing materials as disclosed in Eberle et al. U.S. patent application Ser. No. 08/712,576 filed on Sep. 13, 1996, which is expressly incorporated herein by reference. However, in other embodiments, the transducer array backing material may also be used to support the integrated circuitry in a flexible circuit design of the type disclosed in Eberle et al. U.S. Pat. No. 5,857,974, which is expressly incorporated herein by reference. The probe assembly 24 comprises an array of transducers fabricated from highly sensitive transducer materials of the type previously disclosed in the Eberle et al. U.S. Pat. No. 5,368,037 and the Eberle et al. patent application Ser. No. 08/712,576. In the illustrated embodiment of the invention, the transducers emit 20 MHz ultrasound excitation waveforms. However, other suitable excitation waveform frequencies would be known to those skilled in the art. The transducers of the probe assembly 24 receive the reflected ultrasonic waveforms and convert the ultrasound echoes into echo waveforms. The amplified echo waveforms from the probe assembly 24, indicative of reflected ultrasonic waves, are transferred along a microcable 25 to a signal processor 30 located outside the patient. The catheter 20b ends in a three-part junction 29 of conventional construction that couples the catheter to an inflation source 31, a guide wire lumen and the signal processor 30. The inflation and guide wire ports 29a and 29b, respectively, are of conventional PTCA catheter construction. The third port 29c provides a path for the cable 25 to connect with the signal processor 30 and video display 28 via an electronic connector 33.

It should be noted that the present invention can be incorporated into a wide variety of ultrasound imaging catheter assemblies. For example, the present invention may be incorporated into a probe assembly mounted upon a diagnostic catheter that does not include a balloon. In addition, the probe assembly may also be mounted in the manner taught in Proudian et al. U.S. Pat. No. 4,917,097 and Eberle et al. U.S. Pat. No. 5,167,233, the teachings of which are explicitly incorporated, in all respects, herein by reference. These are, however, only examples of various probe assembly mounting configurations. Other configurations would be known to those skilled in the area of ultrasound catheter probe design.

While a number of techniques and apparatuses will be known to those skilled in the art for obtaining ultrasound image data for depicting dynamic features within a field of view of an ultrasound imaging probe, in a preferred embodiment of the present invention, the color flow system uses information from both static imaging scans and dynamic imaging scans to detect and image moving blood within a vessel. Such scans are respectively referred to herein as B-Scans (Brightness) and F-Scans (Flow). The B-Scans and F-Scans are constructed from a set of received radio frequency (hereinafter "RF") signals known generally as RF A-Scans.

Figure 3:
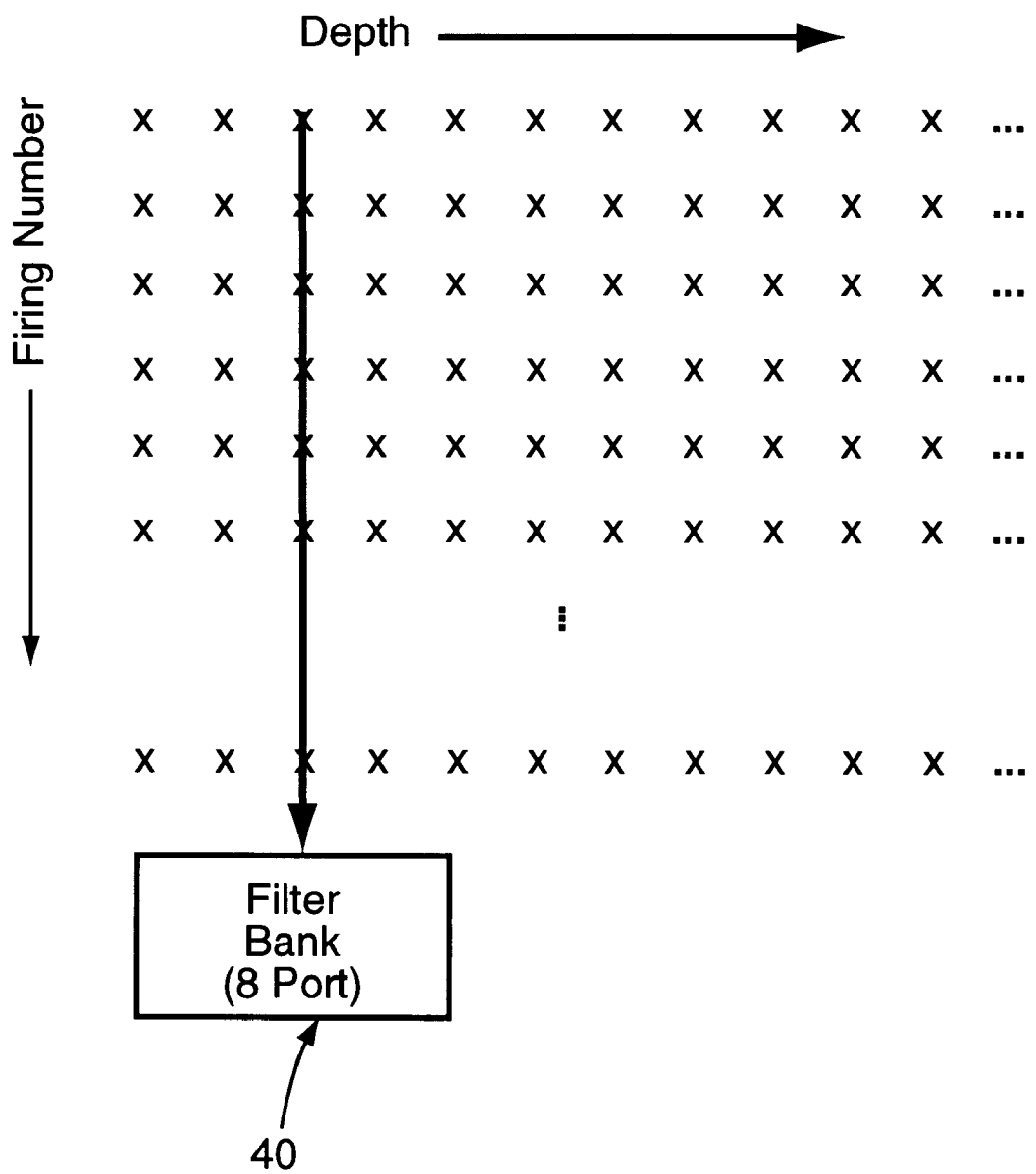
FIG. 3 is a representation of a corner turner approach used to generate a set of dynamic image data for an imaged region.

Turning now to FIG. 3, dynamic image data are initially obtained by means of a multi-port filter bank approach generally described in U.S. Pat. No. 5,453,575, the contents of which are incorporated herein by reference. In the preferred embodiment, during F-Scans eight adjacent array elements act as a single transceiver to fire ultrasonic waves into the vasculature. Unlike other known imaging techniques, multiple measurements, from multiple firings of the transducers at a particular position on the transducer assembly, are made before advancing the active aperture by one element. For each position, all RF A-Scan echoes received during F-Scans are processed in a known manner by an 8-port filter bank 40 to obtain eight (8) different frequency response image signal sets. This signal filtering technique, illustratively depicted in FIG. 3, is known by those skilled in the art as a classic corner turner approach.

In FIG. 3, each "x" represents a single digitized, transduced echo signal reading. Also, each row represents a set of readings at various distances from the set of 8 transducers. In a preferred embodiment, 2048 such readings are taken for a single transducer firing. Finally, each column represents the set of digitized signal readings at a particular depth at a particular transducer firing position.

The eight (8) distinct filters comprising the filter bank 40 produce eight (8) output RF A-Scans for every position within an F-Scan such that each one of the eight (8) output signals from the filter bank 40 represents the signal passed by one of the eight (8) motion filters tuned to produce a signal representative of a particular speed of material within the selected field of view of the ultrasound imaging device. Ideally, the power in each of the eight output signals from the eight filter ports at any given depth represents the flow signal for a blood flow speed range determined by the bandwidth of the motion filter.

Figure 4:
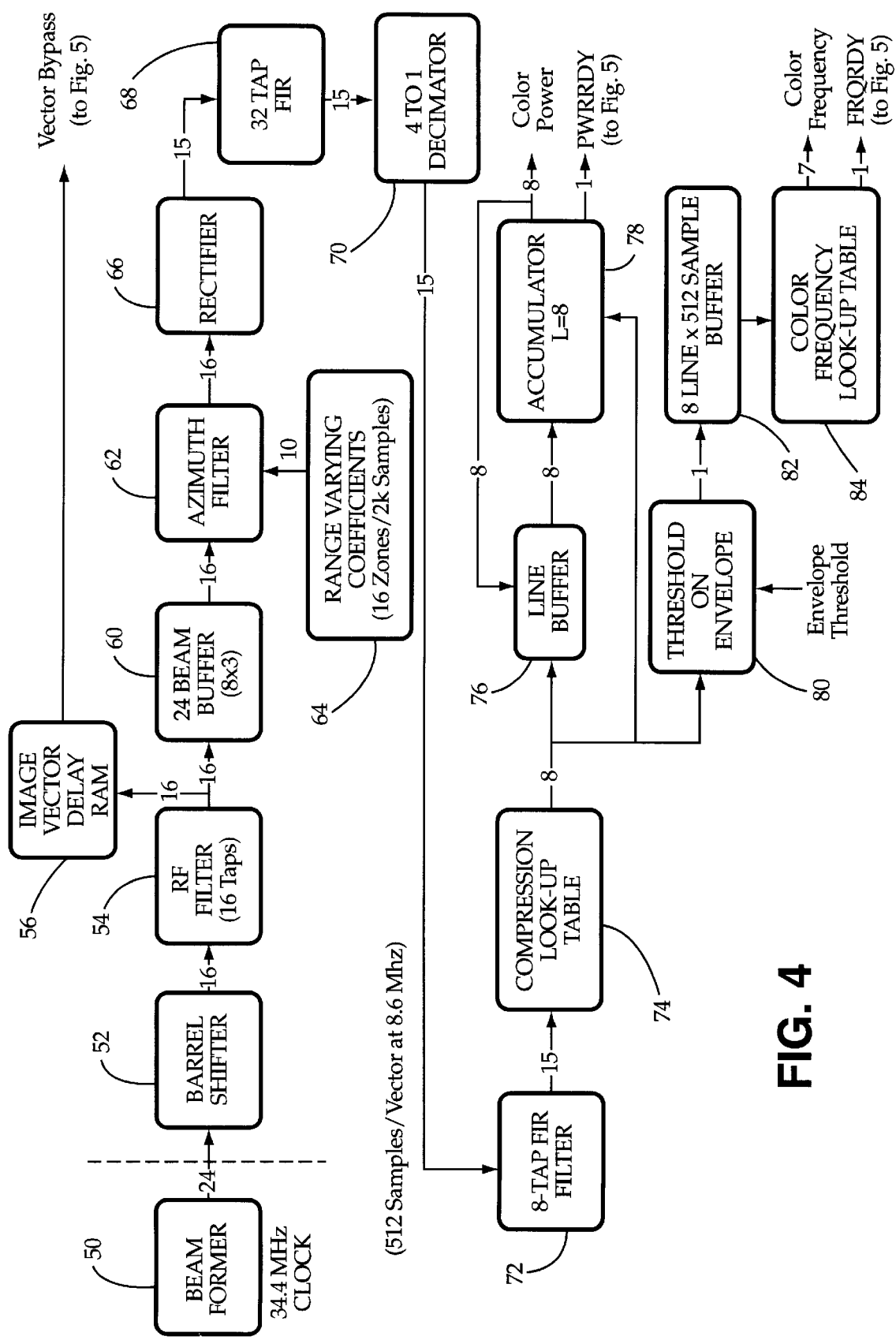
FIG. 4 is a block diagram representation of a first portion of a color flow processor system in accordance with a preferred embodiment of the present invention.

Turning now to FIG. 4, the eight filters are incorporated within a Beam Former 50 operating at a 34.4 MHz clock rate. It is noted however, that in other embodiments of the present invention the Beam Former 50 may comprise more or fewer filters. The presently preferred ultrasound probe includes 64 ultrasound array elements. Thus F-Scans are performed at 64 aperture positions, one for each array element, to produce 512 dynamic imaging vectors. The 512 dynamic imaging vectors consist of eight (8) filtered sets of image data at each of the 64 aperture positions on the preferred 64-element transducer array.

It is further noted that numbers are interposed in the paths connecting the stages of the presently preferred image signal processing and display system. These numbers identify the data path width between the hardware stages. It is noted that such designations are generally design considerations and other path width configurations would be known to those skilled in the art in view of the description of the embodiment contained herein.

The Beam Former 50 is configured to multiplex between F-Scan (motion) and B-Scan (static) measurements, such that separate motion and static image data frames are alternately provided by the Beam Former 50. During B-Scan image data acquisition for a frame, four firings at each aperture position are signal averaged in an Analog to Digital Converter (ADC) board (not shown), and independent measurements are made at all transmit/receive element pairs over the active aperture. The Beam Former 50 is configured for complete data set, i.e., phased array, reconstruction over an active aperture of 14 elements at each of 512 vectors during B-Scan operation. The 512 RF A-Scans output from the Beam Former 50 during B-Scan operation represent 512 beams uniformly distributed around a circle corresponding to a cylindrical ultrasound transducer array. As currently configured for color flow imaging operation, the pulse repetition intervals during B-Scan operation is selected to produce a frame period of about 41.6 msec (24 frame/sec).

The same Beam Former 50 hardware is used during formation of F-Scan frames. However, as previously mentioned above, the hardware is controlled to generate eight (8) sets of motion information at each one of 64 aperture positions. Motion detection image data are obtained by shorting together eight neighboring transducer elements during each one of 64 firings at a single position. Each set of two firings is signal averaged (summed) in the ADC, producing 32 independent signals passed to the Beam Former 50 for motion processing. The Beam Former 50 is described. in O'Donnell et al. U.S. Pat. No. 5,453,575 previously incorporated herein by reference. In order to achieve 24 frame/sec operation, the pulse repetition interval for motion detection frames should be about 10 $\mu$sec.

Figure 5:
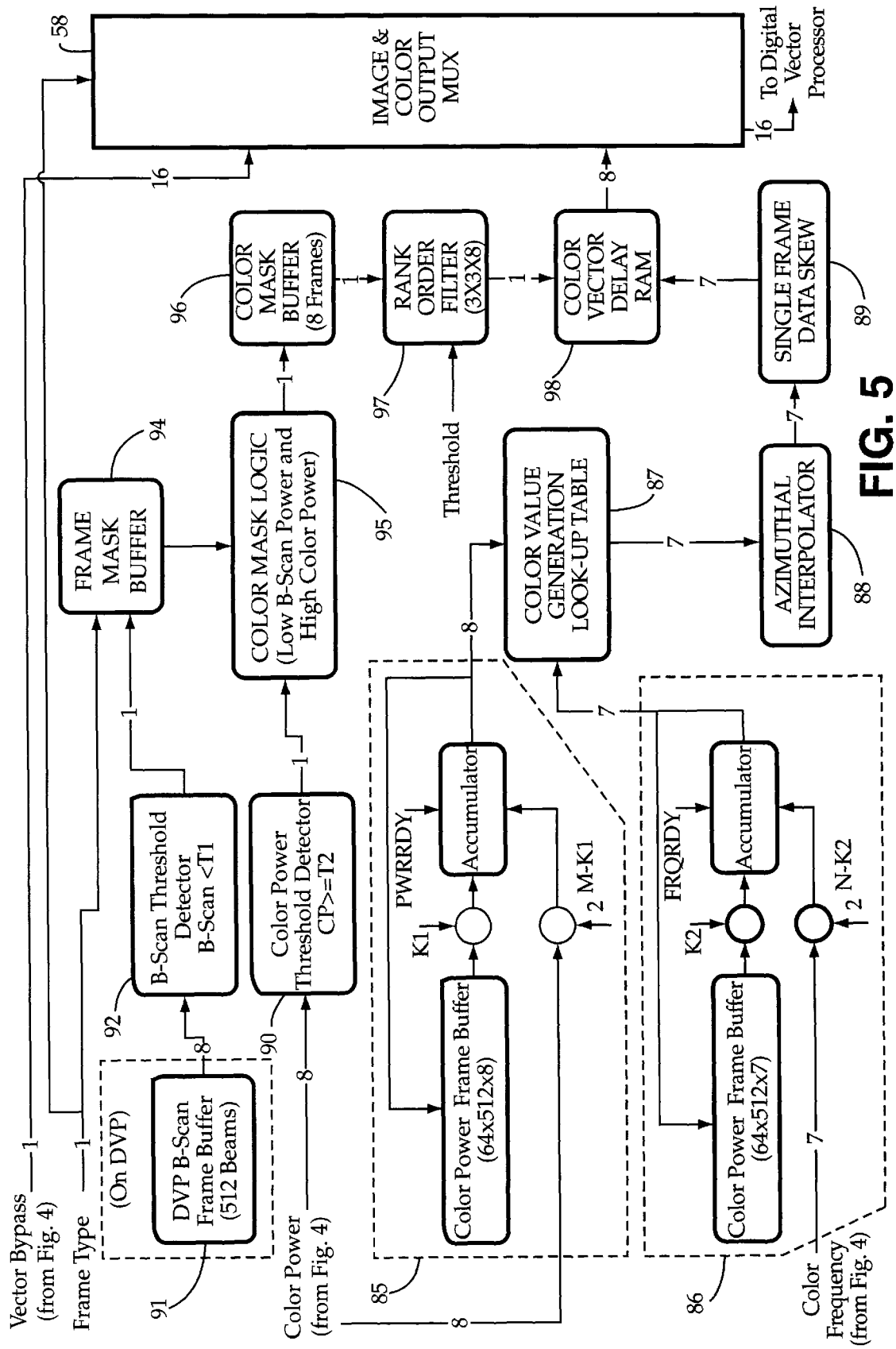
FIG. 5 is a block diagram representation of a second portion of a color flow processor system in accordance with a preferred embodiment of the present invention.

The primary functions of the portion of the flow imaging system illustrated in FIGS. 4 and 5 are to select B-Scan (static image) and F-Scan (motion detection) information from separately generated "flow" and "brightness" scans, and to thereby prodiuce a composite frame representing a 512 vector, spatial representation of blood flow regions in a field of view. This is accomplished by superimposing portions of a flow scan image meeting a flow image signal criteria upon an image constructed from B-Scan data.

Continuing with the description of FIG. 4, a 16-bit Barrel Shifter 52 receives F-Scan or B-Scan data (depending on the mode of operation) directly from the Beam Former 50 at a 34.4 MHz clock rate. As will be appreciated by those skilled in the art, the Barrel Shifter 52 is selectively controlled to bit shift input data in accordance with a set of control inputs. Barrel shifted data are output to a 16 tap Finite 'Empulse Response (FIR) filter 54.

The FIR filter 54 applies programmably selected weights to each one of the 16 taps based upon the scan type. For B-Scan frames, coefficients are applied to the 16 taps to improve the transducer impulse response and reduce axial artifacts seen on strong reflectors such as stent struts. This is accomplished by applying filter coefficients derived by means of well known filtering methods. During F-Scan frame processing, the weights applied to each of the taps of the FIR filter 54 are selected, in a known manner, to narrow the pulse bandwidth around the carrier frequency (nominally 20 Mhz) to both reduce out-of-band-noise created by the eight (8) motion detection filters and improve the overall electronic signal to noise ratio.

The output signals from the FIR filter 54, are de-multiplexed during B-Scan frame processing to an Image Vector Delay RAM 56. Processing flow images is a multi-staged procedure. In order to improve throughput, the flow images are processed in a pipeline. The pipeline processes up to four flow images at a given time. The Vector Delay RAM 56 comprises memory arranged to provide a four-frame memory storage that is refreshed (with new frame data) and read in a round-robin manner. Thus, the Image vector Delay RAM 56 facilitates synchronization of B-Scan frames with F-Scan frames, which as mentioned above are obtained from the Beam Former 50 on an alternating basis. The stored filtered B-Scan data are output to an Image and Color Output Multiplexer (MUX) 58 (depicted on FIG. 5) which selects signals tor input to a digital vector processor (not shown) which performs additional processing on the B-Scan data such as ringdown subtraction and detection. The B-Scan data will ultimately be converted into video pixel coordinates and selectively combined with processed F-Scan image data to generate a composite image displaying a colorized image of flow regions simultaneously with relatively static image features within a field of view.

The output data of the FIR filter 54, corresponding to F-Scan frames, is de-multiplexed to an F-Scan signal processing hardware chain which is separate and distinct from the B-Scan image signal processing chain. The F-Scan signal processing chain is illustratively depicted in the remaining portion of FIG. 4 and creates a set of color (motion) power data and a set of color (motion) frequency data for each image point in an F-Scan frame. Initially, the de-multiplexed F-Scan data are received by a Beam Buffer 60.

An azimuthal FIR filter 62 reduces artifacts associated with beam forming in F-Scan frames arising from shorting eight (8) adjacent transducer elements together which results in a less focused aperture. In the preferred embodiment, the azimuthal FIR filter 62 includes 3 taps to perform beam smoothing across three (3) adjacent aperture positions (beams) for each set of filter bank data. Since eight (8) filter bank data sets are associated with each aperture position, the Beam Buffer 60 is dimensioned to store 8×3 sets of beam data.

A set of Range Varying Coefficients 64 are applied to the azimuthal FIR filter 62 during processing of the 8×3 beams to compensate for range (distance) dependent azimuthal beam forming artifacts in a manner known to those skilled in the art. In the preferred embodiment of the present invention, the values of the Range varying Coefficients 64 are modified up to 16 times over the entire 2048 data points within a beam. It is noted that while the azimuthal filter stage represented by the Beam Buffer 60, the azimuthal FIR filter 62 and the range varying coefficients 64 are desirable, this stage is not present in another embodiment of the invention.

Following azimuthal filtering, the color flow processing system detects all 512 RF A-Scans constituting an F-Scan frame. After a rectifier 66 processes the 512 F-Scan beams received from the azimuthal FIR filter 62, the rectified output is provided to an FIR filter 68 that integrates the received data and passes the filtered data to a decimator 70. The 4:1 decimation reduces the clock rate of the data from 34.4 MHz to 8.6 MHz and the total length of each beam from 2048 points to 512 points. The 8.6 MHz output rate matches the output rate of a digital vector processor (DVP) described hereinbelow.

In contrast to B-Scan data, detected motion signals usually benefit from additional axial smoothing to improve the signal to noise ratio. Consequently, the output data from the decimator 70 is received by an 8 tap FIR filter 72 that provides additional filtering along each beam. The output of the 8 tap FIR filter 72, is received by a compression look-up table (LUT) 74 which reduces the bit density from 16 to 8 bits. The form of amplitude mapping is merely a design choice and includes linear mapping and logarithmic mapping as two viable alternatives.

The compressed data is routed to two distinct flow image processing sub-systems which calculate a signal power (motion power) and a flow speed (motion frequency) for each image point based upon the compressed F-Scan data received from the compression LUT 74. Because the flow information is displayed as a color image, the signal power (motion power) and flow speed (motion frequency) are referred to herein as "color power" and "color frequency" respectively.

The color power represents an estimate of the signal strength within a motion pixel. In conventional color Doppler (which in fact may incorporate the present invention), this signal is equivalent to the area under the curve of the Doppler spectrum. To approximate this power under the present invention, the detected outputs of the filter bank are summed over all eight (8) sets of data for a particular aperture position corresponding to the eight (8) filter bank bins. An eight line buffer 76 and an accumulator 78 perform the summing operation on the compressed F-Scan data. While not shown in the drawings, the accumulator 78 output is normalized by bit shifting the accumulated output 3 bits to render an 8 bit value (color power) that is received by further color image processing hardware illustratively depicted in FIG. 5.

Note that the details of the compression LUT 74 affect the sum obtained in the accumulator. If pure logarithmic compression is used, then the sum over the 8 filter bank data sets for a particular aperture is equivalent to a product over the detected filter outputs. Conversely, if linear compression is used, then all 8 filter bank data sets are simply added thus increasing the influence of noisy filter outputs having low flow amplitudes. Thus, an appropriate compression function must be carefully selected so that the sum over filter banks approximates the area under the curve of a Doppler spectrum.

Before describing the circuits for generating "color frequency" values for F-Scan frames, it is noted that, indeed, detected motion F-Scans also can be used to estimate the speed of flowing blood. This is, of course, a very complicated problem because flow at the same speed can show up in different filter bank bins based on a number of factors, including: flow direction (in-plane versus out-of-plane), local speckle characteristics, filter leakage, and noise. One method to differentiate between fast flow and slow flow is to count the number of filter bank bins above an established noise threshold.

Furthermore, because each filter in the bank may have slightly different characteristics, especially the filter closest to zero frequency, the noise threshold is independently set for each filter bank bin. At every range sample, each of the eight (8) filter bank signals is compared in a Threshold On Envelope 80 and a logic 1 is assigned to each of the eight (8) filter bank signals exceeding the threshold value provided by an adjustable Envelope Threshold signal input. The resulting 8-bit result of the threshold comparison is stored in an 8×512 (single, decimated beam) buffer 82. Each bit in the 8bit word represents the output of the threshold test for a corresponding filter bin. Each of the 8-bit words is used to access an entry in a Color Frequency LUT 84. In an embodiment of the present invention the programmed entries of the Color Frequency LUT 84 nominally estimate the flow (motion) frequency by counting the number of bits set in each input word. That is, the more bits set, the higher the flow velocity. Other, more advanced Color Frequency LUTs will likely comprise complicated algorithms since many different types of patterns can be expected for very similar flow conditions which are best resolved by clinical trials under a wide range of conditions.

FIG. 5 schematically depicts signal processing hardware programmably controlled to combine color (motion) power, color (motion) frequency and. B-Scan frame data into a single flow estimate. In accordance with one aspect of a preferred embodiment of the present invention, signal stability is achieved for both the color power and color frequency values over time by means of single feedback Infinite Impulse Response filter/buffers 85 and 86 respectively. Each filter/buffer 85 and 86 includes a 64×512×(1 word) buffer for storing the previously calculated values for an entire F-Scan frame. Color Power Persistence Coefficient K1 and its associated coefficient M provide a first persistence factor. Color Frequency Persistence Coefficient K2 and its associated coefficient N provide a second persistence factor. In accordance with an aspect of the new imaging system, the first and second persistence factors are independently designated.

It is noted that in the above described embodiment, the first and second persistence factors are each established by a combination of two variables. In other embodiments of the invention, the first and second persistence factors may consist of single adjustable variables or other combinations of variables—even variables common to both filters. An example of such a system is the instance when "M" and "N" are the same value.

The operation of the accumulators within filter/buffer 85 and filter/buffer 86 is synchronized with the input values on the lines labeled "Color Power" and "Color Frequency" by means of control lines "PWRRDY" AND "FRQRDY" from the accumulator 78 and the Color Frequency LUT, respectively. The structure, function and operation of the filter/buffers 85 and 66 will be known to those skilled in the art.

A relatively long term persistence value (favoring little change from a previous calculated value) should be designated for color power signal filtering (via proper designations of values for K1 and M) since this value should not fluctuate much over the cardiac cycle because it is a measure of the scattering coefficient from moving blood. Color power, therefore, should be averaged over long periods, compared to the cardiac cycle, to smooth noise and speckle fluctuations. The color power coefficient K1 and the value "M" are generally selected to provide a persistence period of approximately 1 second. The first persistence factor, determined in the preferred embodiment by the values of K1 and M, is adjustable to facilitate adjustment by a user during both testing and use on a patient.

In contrast, color frequency is expected to change over the cardiac cycle because it is related to flow speed. Thus, values for K2 and N are designated to accomplish the time-based smoothing with a persistence period shorter than a heartbeat. The color frequency persistence factor determined by the coefficient K2 and the value "N" are generally selected to provide a color frequency persistence period of 40–100 milliseconds. The second persistence factor, determined in the preferred embodiment by the values K2 and N, is adjustable to facilitate adjustment by a user during both testing and use on a patient.

The combined frame averaged 8-bit color power and 7 bit color frequency signals are provided by accumulator outputs from the filter/buffers 85 and 86 respectively to a Color Value Generation (CVG) LUT 87. The CVG LUT 87 combines motion power and motion frequency information to produce a 7 bit color signal having both color and brightness coefficients. As in the case of the Color Frequency LUT 84, the CVG LUT 87 can be programmed in many ways, e.g., ignore motion frequency information and produce only a motion power signal, create a sigmoid threshold on the power signal to control luminance and vary color according to the color frequency value, etc. The designation of particular output values for specified inputs to the CVG LUT are primarily design considerations which may bet resolved by clinical trials.

The CVG LUT 87 outputs a single color signal to an azimuthal interpolator 88. F-Scan imaging vectors are produced on 64 beams; whereas, B-Scans use 512 beams. The azimuthal interpolator 88 creates 512 beams from the 64 provided beams using standard linear interpolation. Linear interpolation is adequate because the azimuthal radiation pattern associated with 8 elements tied together is likely quite broad, even with azimuthal filtering of RF data before flow processing. The interpolator 88 transmits the resulting interpolated image data to a single frame flow data skew 89 where the data is buffered and time skewed to produce the 7 bit color value signal appropriate for output to a Digital Vector Processor (DVP) and subsequently to a scan converter which is not shown but is described in the O'Donnell et al. U.S. Pat. No. 5,453,575.

The top path of FIG. 5 schematically depicts the image processing hardware for logically comparing F-Scan color power and B-Scan signal levels to produce a 1 bit color mask indicating whether a point on a particular beam in the final 512×512 flow frame should be designated as a color flow image point. The single bit mask designates the source (B-Scan or F-Scan) and manner of displaying (gray scale or color) a particular image point on the 512 beams comprising 512 points each. The signal processing schematically depicted along the top path of FIG. 5 significantly reduces "flashing"—that is, the seemingly random turning on and off of color pixels during the display of a composite flow/static tissue image.

A color power threshold detector 90 compares the color power signal output from the accumulator 78 to a designated threshold level T2 to produce logic signal B. Logic signal B is 1 if the color power signal meets or exceeds the threshold level and 0 if the color power signal is below the threshold level. If logic signal B is 1, then the point is identified as a potential color flow image point. If logic signal B is 0, then a particular image point is not dynamic (as determined by the comparison to T2) and therefore is designated to display B-Scan data.

In parallel to the color power level detection, B-Scan data (512 beams) input from a B-Scan data buffer 91 of the DVP are compared to a threshold level. T1 at B-Scan threshold detector 92. The logic signal produced by the B-Scan threshold detector 92 is 1 if the B-Scan value for an image point is below a designated threshold level and 0 if it is above the threshold (indicating a region of tissue). If this bit is 1, then the B-Scan level is low and the point is identified as a possible blood flow region. A frame identification signal connected to the "enable" input of a Frame Mask Buffer 94 selectively passes the threshold signal provided by the B-Scan threshold detector 92 to the Frame Mask Buffer 94 to ensure that only B-Scan data is involved in producing logic signal A stored in the Frame Mask Buffer 94.

For a given image point within an image, "color flow" status is designated when both signals A and B are logic 1. That is, an image point must have both significant motion (color) power and low B-scan intensity for it to be identified as blood. Logic signal A, however, is on a 512 beam by 512 image point/beam grid; whereas, logic signal B is on a 64 beam by 512 image point/beam grid. Therefore, the 64 input "B" beams to a Data Skew and Comparator 95 are expanded by replicating each of the 64 logic signal beams 8 times and then performing a logical AND operation between the logic signal A beams and the skewed logic signal B beams. The result of the above described processing is stored in a Color Mask Buffer 96.

Note that the color power threshold decision is performed before the color power signal is frame averaged by the filter/buffer 85 in order to prevent spatial smearing of flow information (i.e., in a moving environment, temporal averaging also space averages). If the flow mask information stored within the Color Mask Buffer 96 were to be derived from temporally averaged color power data from the filter/buffer 85, then wall-lumen interfaces would likely blur. To avoid this problem, the color mask is computed in real-time in order to assure spatial alignment between B-Scan and color information provided to the Data Skew and Comparator 95.

The color mask information stored within the Color Mask Buffer 96 may include much noise because it is estimated on a frame by frame basis. Noisy color mask data, in turn, produces color flash artifacts. To reduce the incidence of color flash artifacts, color mask data from the Data Skew and Comparator 95 for the preceding eight (8) B-Scan and F-Scan frames is buffered in the Color Mask Buffer 96. A Space-Time rank order filter 97 filters the color bit mask data offer space (centered around an image point of interest) and most recent color mask frames generated by the system.

Generally, a linear filter, such as a low pass filter, reduces flash artifacts, but also blurs wall-lumen edges. In contrast, a non-linear rank order filter, such as for example a median filter, reduces the likelihood of popcorn noise (flashes) in either space or time while preserving both spatial and temporal edges. The Space-Time rank order filter 97 generates an output bit mask by applying a 3×3×8 space-frame filter to the data stored in the Color Mask Buffer 96. A spatial, L=8 comb is used to filter over the same spatial extent as the original color data for 8 frames.

Figure 6:
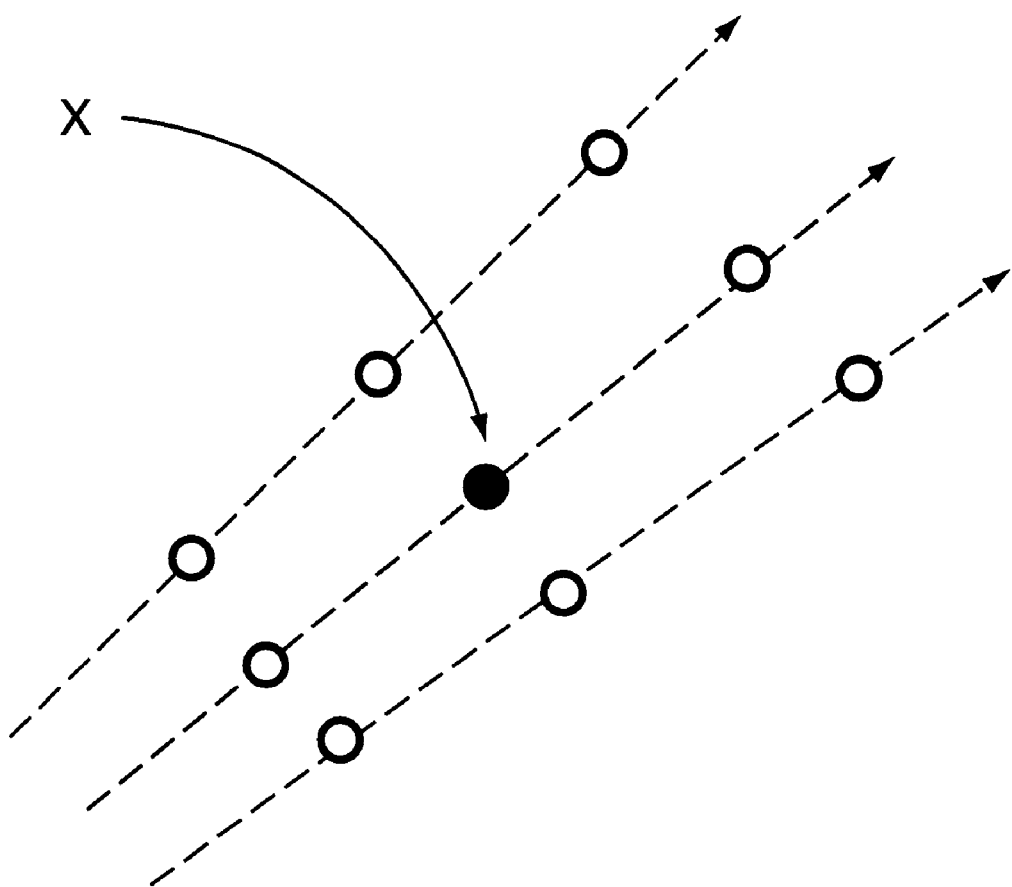
FIG. 6 is an illustrative depiction of a set of 3×3 image points that are sampled in the course of color mask space-time filtering in accordance with an aspect of the present invention.

Turning briefly to FIG. 6, the 3×3 space referenced on a single image frame during the space-time filtering is illustratively depicted. As shown in the figure, a first set of three points are referenced from a first radial beam containing the current image point X and two adjacent image points. The remaining six image points are referenced (3 each) from two adjacent beams at distances corresponding to the three points on the first radial beam.

The value of a particular mask bit in the 512 beam by 512 points/beam bit mask is obtained by summing the values of the bits contained within the 3×3×8 space-time "volume." A maximum value for the summed bits is seventy-two (72). In a particular embodiment the rank order filter 97 is configured as a median filter. In this particular embodiment, if the summed value of the mask bits is equal to or greater than a threshold value of thirty-six (36), then the rank order filter 97, acting as a median filter, outputs a logic one (1) value for the mask bit, thereby indicating that the particular image point is to be colorized.

It is noted that while a 3×3 spatial kernel has been selected, other suitable spatial kernels may be utilized to provide more robust filtering. The choice of eight (8) frames of mask data is a presently favored choice for time filtering, but other values are contemplated to fall within the scope of the present invention. Finally, the choice of a threshold of thirty-six (36) (i.e., one-half the maximum—and thus a median filter) for the rank-order filter 97 may be modified in accordance with the needs or preferences of a particular clinical operation or imaging system hardware by means of a THRESH signal input.

When the threshold is modified to a value other than the median value, while still a "rank order" filter, this filter is generally considered not to be a "median" filter since the determining point would not be the middle of the range of values. Of course in instances where the selected threshold value is substantially the same as the median value, one may refer to such a filter as a "substantial median filter."

For each of the 512 image beams and each one of the 512 image points on a single image beam, a Color Vector Delay RAM 98 combines the single bit of color mask data provided by the Space-Time rank order filter. 97 and the 7-bit color value data from the single frame flow data skew 89 to generate a color image frame. The color image data points of the color image frame are each stored as an 8-bit word. The output of the CVD RAM 98 acts as one data input to an Image and Color Output Multiplexer (MUX) 58. The other data input to the Image and Color Output Mux 58 is the 16 bit B-Scan data from the FIR filter 54 and image vector delay RAM 56 of FIG. 4, i.e., the Vector Bypass signal.

Using a Color Frame control signal to determine which data type (B-scan or color flow) to pass, the output of the MUX 58 is passed to the DVP. If a color frame is selected, then the DVP passes the processed color image data stored within the Color Vector Delay RAM 98 to the display processor. Alternatively, if a color frame is not selected, then the DVP takes the RF filtered raw B-Scan data and processes it (i.e., decimates the 2,048 beam samples into 512 samples) and passes the B-Scan data to the display processor for scan conversion, etc. The decimated B-Scan data is stored in the B-Scan data buffer 91.

Current DVPs process B-Scan data and pass the resultant to the display processor for scan conversion and display. The DVP according to the invention, receives both raw B-Scan and processed color flow frames. As mentioned above, the DVP processes raw B-Scan data if the color frame bit is logic 0 by decimating the input A-Scan data into 512 samples per beam for each of the 512 beams. The processed B-Scan data are then passed on to the display processor. If the Color Frame control bit equals logic "1", then Color frame data are passed directly from the Color Vector Delay RAM 98 to the display processor without processing by the DVP.

Both frame types are buffered and their location followed throughout the entire processing chain. That is, consecutive B-Scan and color frames entering the display processor should be temporally aligned. The display processor separates and independently buffers color flow and B-Scan frames. For every output pixel after scan conversion (from beams to pixels), the color bit specifies whether to display the color value according to a color map or the B-Scan value according to a gray scale map.

It should be noted that the color bit is not scan converted using a linear operation such as bi-linear interpolation. For each output pixel displayed on a rectilinear grid, a simple logic operation should be performed on the color bits for the associated nearest neighbor pixels on the polar grid to decide if the output pixel is color or gray scale.

Figure 7:
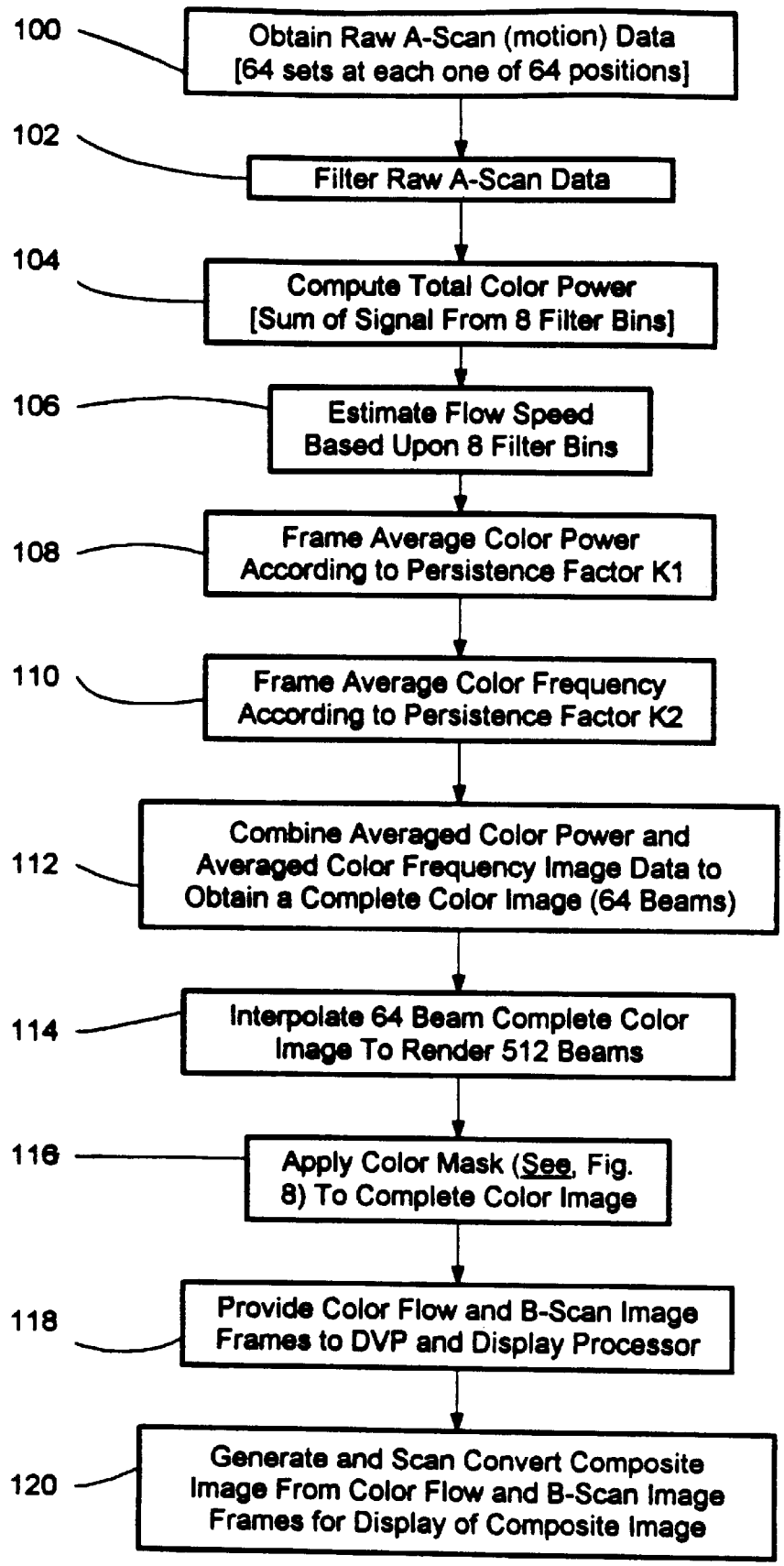
FIG. 7 is a flowchart summarizing the steps performed by an imaging system including a color flow processor for creating a composite brightness-flow image of an imaged blood vessel in accordance with a preferred embodiment of the present invention.

Having described system hardware and the functions performed by the hardware in order to generate, for later display, a color flow image during ultrasound intravascular imaging, attention is now directed to FIG. 7 which summarizes the steps performed by this ultrasound imaging system to generate the color flow image based upon ultrasound echo information. At some point prior to generating a color mask, a B-Scan (static image) frame is obtained in close temporal proximity to the F-Scan (motion image) frame. It is noted that while the steps are ordered in a particular manner to facilitate a description of the preferred embodiment of the present invention, those skilled in the art will readily appreciate that with respect to a number of the steps described below, the order in which the steps are performed is not restricted to the illustrative order depicted in the flowcharts.

At step 100, the ultrasound imaging system acquires raw digitized RF A-Scan data. Sixty-four (64) echo samples (2048 points) are taken at each of 64 positions along the perimeter of an ultrasound transducer assembly. Next, at step 102 these F-Scan data are filtered by the color flow processor hardware schematically depicted in FIG. 4 in order to reduce noise in the color flow raw data.

At step 104, the buffer 76 and accumulator 78 receive color flow data and sum the motion power for image points over the eight motion frequency bins in order to obtain a total color power for each image point. During step 106, a threshold envelope is applied to the same color flow data processed during step 104 in order to estimate the flow speed from the eight (8) sets of image point data corresponding to the eight (8) filter bins. After threshold processing, the resulting data are applied to a color frequency LUT 84 to render a color frequency value for each image point.

In accordance with a particular aspect of the new imaging method, during step 108 the color power data obtained during step 104 are frame averaged. In other words, the color power data of the present frame are combined with a previous averaged color power data set to render a new averaged color power data set. The contribution of the new color power data to the averaged color power data is determined by a first persistence factor which is determined by values for the coefficient K1 and the value of M. The first persistence factor is preferably selected to filter short term changes since the color power should be relatively stable over short periods of time.

During step 110 the color frequency data obtained during step 106 is combined with a previous averaged color frequency data set to render a new averaged color frequency data set. The contribution of the new color frequency data to the averaged color frequecy data is determined by a second persistence factor which is determined by values for the coefficient K2 and the value of N. The second persistence factor is designated independently from the second persistence factor, thereby enabling a user to specify a value for the second persistence factor which enables the average color frequency to pass short term changes thereby enabling a user to observe variations in blood flow speed during the different stages of a cardiac cycle. The values for K2 and N, in combination and applied to a filter as illustrated in FIG. 5, specify a signal persistence period significantly smaller than the persistence period specified by the first persistence factor.

Next, during step 112 the averaged color power and averaged color frequency data are combined for each image point over a color flow frame and submitted to the color value look-up table 87 in order to render a color image approximation. The color image approximation includes both color and brightness values for each image point. However, since these data are only specified for 64 beams extending from a circular perimeter corresponding to an ultrasound transducer assembly, at step 114 the 64 beams are interpolated to 512 beams in advance of scan conversion of the beams into display coordinates.

Figure 8:
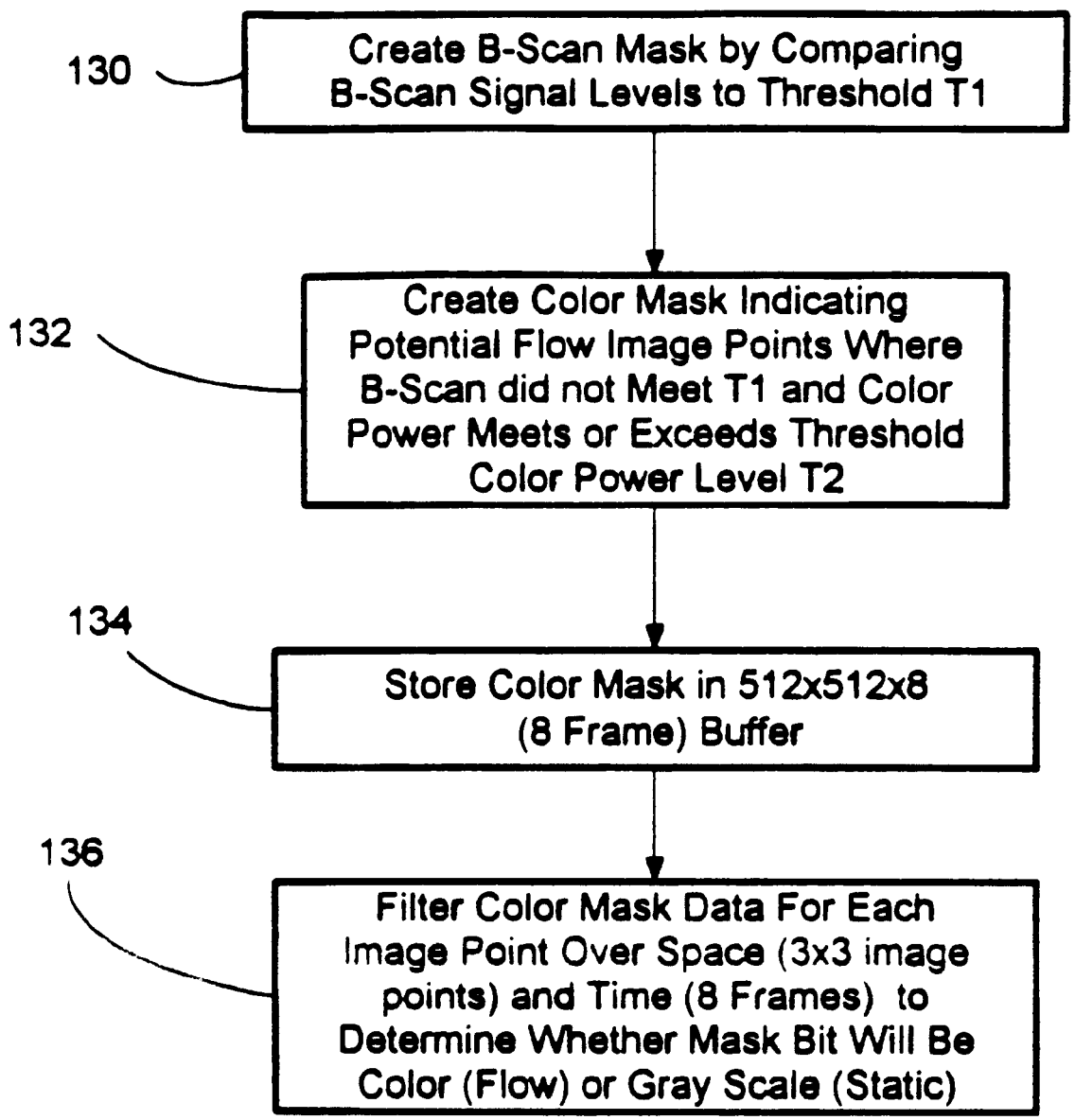
FIG. 8 is a flowchart summarizing the space-time filtering operations performed by the image processing system of the present invention in order to reduce noise and color flashing in a displayed image.

At step 116, a color mask for the current frame generated by the color flow processor in accordance with the sub-steps summarized in FIG. 8 is applied to the color flow image data computed by the azimuthal interpolator 88 (during step 114). Applying the color mask to the azimuthal interpolated color flow data renders a color flow image that specifies Eor each particular image point whether to use the dolor flow image data (if the color mask specifies "flow data") or alternatively to use the gray scale static image data computed from B-Scans (i.e., disregard the computed color flow data for this particular image point) if the color mask specifies "static data".

At step 118 the Image and Color Output MUX 58 selectively passes either color flow (F-Scan) image frame data or raw, static (B-Scan) image frame data to the Digital Vector processor based upon the value of the Color Frame control signal. In the case of a color flow image frame, the DVP passes the data on to the display processor for further output processing. In the case of B-Scan image frame designation, the DVP detects the RF A-Scans and decimates the resultant signal to produce a 512 sample beam for each of the 512 beams constituting a B-Scan frame. Thereafter, the DVP stores the 512 beams in the B-Scan frame buffer 91 and passes the processed B-Scan image data on to the display processor.

Next, at step 120, the display processor combines the buffered, processed B-Scan and Color Flow images received during step 118 into a composite image. This is achieved by using every image point from the Color Flow image point having its color bit turned "on" to indicate that the particular image point is to be displayed in color. All the remaining images points are filled in using the corresponding image data from the B-Scan image frame. It is noted that the B-Scan image is synchronized with the color flow image, by means of the Image Vector Delay RAM 56, in order to ensure that the two sets of image data correspond to raw image data acquired within a very short same time period (e.g., adjacent frame periods).

Display processing of the composite Color Flow/B-Scan image continues during step 120 with the conversion of the composite image points from polar coordinates to display pixel coordinates for output upon the display 28. For every output pixel after scan conversion, the color bit specifies whether to display the color value according to a color map or the B-Scan value according to a gray map. The scan conversion is not a linear operation, such as bilinear interpolation. Instead, for each pixel, the color bits for the nearest neighbors on the polar grid are observed to determine whether to designate the output pixel as color or gray scale. At this point, display processing is complete and the composite image is presented upon the display 28. It is further noted that the steps 100 to 120 are performed with sufficient speed to present a substantially real-time image of a region, such as an imaged coronary vessel.

Turning now to FIG. 8, the steps are summarized for filtering color mask bits in both space and time in order to eliminate color "flash." During step 130, the B-Scan threshold detector determines for a frame of B-Scan image point data whether the signal level for each particular image point is too high to represent blood flow. If the B-Scan signal reaches a specified threshold (T1), then the image point is designated "color off" to indicate that the particular image point is likely not blood. This comparison is performed for all B-Scan data and stored in a 512 beam by 512 point/beam buffer.

At step 132 a color mask is constructed for a frame wherein a mask bit is designated "color" for a particular point if the B-Scan signal level did not meet the T1 threshold and the color power meets or exceeds the color power threshold T2. Otherwise the mask bit for the particular point is set to "no color."

Next, at step 134 the mask bits are stored in a color mask frame buffer. Such color mask frames are buffered for a current as well as a set of previous frames. In the preferred embodiment of the present invention, the total number of color mask frames buffered equals eight (8).

In accordance with a particular aspect of the present invention, during step 136 the buffered color mask data is filtered in space and time to render a filtered color mask designating whether a particular image point is a color flow image point or alternatively a gray scale static image point. In a preferred embodiment of the present invention, the spatial extent for a particular image point comprises the point of interest and each one of its eight (8) adjacent neighbors (in a plane). In addition to the two dimensional plane rendering nine (9) color mask bits, the filtering occurs over time by including the eight (8) most recently rendered color masks stored in the color mask buffer 96.

The preferred filtering method comprises summing the values represented in the 3×3×8 time-space region and comparing the result to a median value 36 or some other specified threshold in order to determine whether to designate "color on" or "color off" for the image point of interest. The resulting filtered image point is provided for further image processing as described in step 116 above.

While the invention has been described in connection with certain preferred embodiments, there is no intent to limit it to those embodiments. On the contrary, the present invention is applicable to other imaging methods which provide a combination of dynamic and static image data. For example, the present invention may be advantageously incorporated into an imaging system wherein the dynamic and static image data is obtained via Doppler imaging techniques. The intent is to cover all alternatives, modifications, and equivalents included within the spirit and scope of the invention as defined by the appended claims.

What is claimed is:

1. A method for generating a color image of a field of view within a patient based upon image data having both motion frequency and motion power components, and adjustable first and second feedback persistence factors, wherein motion frequency is represented in the form of designated colors and motion power is represented in the form of brightness levels, the method comprising the steps of:

first generating instantaneous motion power data corresponding to the imaged field of view;

second generating instantaneous motion frequency data corresponding to the imaged field of view;

setting the adjustable first feedback persistence factor to establish a first persistence period that is relatively long in comparison to a cardiac cycle for the patient;

setting the adjustable second feedback persistence factor to establish a second persistence period that is relatively short in comparison to a cardiac cycle for the patient;

first computing a time averaged motion power from a feedback averaged motion power, the instantaneous motion power, and at least the adjustable first feedback persistence factor;

second computing a time averaged motion frequency from a feedback averaged motion frequency, the instantaneous motion frequency, and at least the adjustable second feedback persistence factor;

combining the time averaged motion power and time averaged motion frequency to define a color image; and generating an image for display on a visual display device in accordance with the color image.

2. The method of claim 1 wherein the generating an image step comprises formulating a set of enablement data for selectively determining whether to display image points of the color image in the image for display on the display device.

3. The method of claim 2 wherein the generating an image step comprises using image point data arising from static imaging scans at each image point where the enablement data specifies that the color image data for the image point is not enabled.

4. The method of claim 1 further comprising assigning image signal states, corresponding to a display characteristic, to designated image points with n a field of view, the image signal states being one of at least two potential signal states, said step of assigning image signal states including, for each one of the designated image points, the sub-steps of:

summing image point values corresponding to display characteristic states for a set of image points proximate to the one of the designated image points for a current image frame and for a set of image frames generated in a period of time proximate to the current image frame, to obtain a time and space averaged value for the display characteristic state of the one of the designated image points;

comparing the time and space averaged value to at least one threshold value to render a time and space averaged display for the one of the designated image points; and calculating a display image signal for the one of the designated image points based at least partially upon the time and space averaged display characteristic state for the one of the designated image points.

5. The method of claim 4 wherein the display characteristic state designates whether the designated image point will be displayed in color.

6. The method of claim 5 wherein the color/non-color characteristic for each image point is represented by a single binary bit.

7. The method of claim 4 wherein the set of image points proximate to the designated image point includes substantially each image point adjacent to the designated image point on the current image frame and the set of proximate image frames.

8. The method of claim 4 wherein rank order filtering is applied during the comparing step to assign a signal state based upon a designated range of values associated with particular ranks.

9. The method of claim 8 wherein the rank order filtering is, in particular, median filtering.

10. The method of claim 4 further comprising the sub-step of:

rendering a current display characteristic state for the designated image point, the rendering step including at least the step of comparing a current value associated with the designated image point to a first threshold value.

11. A method for assigning an image signal state, corresponding to a display characteristic, to a designated image point within a field of view, the image signal state being one of at least two potential signal states, said method including the steps of:

rendering a current display characteristic state for the designated image point, the rendering step including at least the step of comparing a current value associated with the designated image point to a first threshold value;

summing image point values corresponding to the display characteristic states for a set of image points proximate to the designated image point for a current image frame and for a set of image frames generated in a period of time proximate to the current it image frame, to obtain a time and space averaged value for the display characteristic state of the designated image point;

comparing the time and space averaged value to at least a second threshold value to render a time and space averaged display characteristic state for the designated image point; and calculating a display image signal for the designated image point based at least partially upon the time and space averaged display characteristic state for the designated image point.

12. The method of claim 11 wherein the display characteristic state designates whether the designated image point will be displayed in color.

13. The method of claim 12 wherein the color/non-color characteristic for each image point is represented by a single binary bit.

14. The method of claim 11 wherein the set of image points proximate to the designated image point includes substantially each image point adjacent to the designated image point on the current image frame and the set of image frames generated in a period of time proximate to the current image frame.

15. The method of claim 11 wherein the set of image points proximate to the designated image point consists of each image point adjacent to the designated image point on the current image frame and the set of image frames generated in a period of time proximate to the current image frame.

16. The method of claim 11 wherein the set of image frames referenced during the summing step comprises a set of N temporally adjacent image frames.

17. The method of claim 16 where N equals about 8 image frames.

18. The method of claim 11 wherein each image point of each frame used to compute the time and space averaged value for the designated image point is given equal weight during the summing step.

19. The method of claim 11 wherein rank order filtering is applied during the comparing step to assign a signal state based upon a designated range of values associated with particular ranks.

20. The method of claim 19 wherein the rank order filtering is, in particular, median filtering.

21. A flow image processor for generating an image of a field of view within a patient based upon image data having both motion frequency and motion power components wherein motion frequency is represented in the form of designated colors and motion power is represented in the form of brightness levels, the processor comprising:

means for generating instantaneous motion power data corresponding to the imaged field of view;

means for generating instantaneous motion frequency data corresponding to the imaged field of view;

an adjustable first feedback persistence factor establishing a first persistence period that is relatively long in comparison to a cardiac cycle for the patient;

an adjustable second feedback persistence factor establishing a second persistence period that is relatively short in comparison to a cardiac cycle for the patient:

a motion power filter for computing a time averaged motion power from a feedback averaged motion power, the instantaneous motion power, and at least the adjustable first feedback persistence factor;

a motion frequency filter for computing a time averaged motion frequency from a feedback averaged motion frequency, the instantaneous motion frequency, and at least the adjustable second feedback persistence factor;

a color image data generator for combining the time averaged motion power and time averaged motion frequency to define a color image; and means for generating an image for display on a visual display device in accordance with the color image.

22. The flow image processor of claim 21 wherein the means for generating an image comprises means for formulating a set of enablement data for selectively determining whether to display image points of the color image in the image for display on the display device.

23. The flow image processor of claim 22 wherein the means for generating comprises means for inserting image data arising from static imaging scans at each image point where the enablement data specifies that the color image data for the image point is not enabled.

24. The flow image processor of claim 21 further comprising a time-space filter for assigning image signal states, corresponding to a display characteristic, to each designated image point within a field of view, the image signal states being one of at least two potential signal states, said time-space filter including:

means for summing image point values corresponding to display characteristic states for a set of image points proximate to a one of the designated image points for a current image frame and for a set of image frames generated in a period of time proximate to the current image frame, to obtain a time and space averaged value for the display characteristic state of the one of the designated image points;

means for comparing the time and space averaged value to at least one threshold value to render a time and space averaged display for the one of the designated image points; and calculating a display image signal for the one of the designated image points based at least partially upon the time and space averaged display characteristic state for the one of the designated image points.

25. The flow image processor of claim 24 wherein the display characteristic state designates whether the designated image point will be displayed in color.

26. The flow image processor of claim 25 wherein the color/non-color characteristic for each image point is represented by a single binary bit.

27. The flow image processor of claim 24 wherein the set of image points proximate to the designated image point includes substantially each image point adjacent to the designated image point on the current image frame and the set of proximate image frames.

28. The flow image processor of claim 24 wherein rank order filtering is applied by the means for comparing to assign a signal state based upon a designated range of values associated with particular ranks.

29. The flow image processor of claim 28 wherein the rank order filtering is, in particular, median filtering.

30. The flow image processor of claim 24 further comprising:

means for rendering a current display characteristic state for the designated image point, the means for rendering comprising a first comparator for comparing a current value associated with the designated image point to a first threshold value.

31. An image processor space-time filter for assigning an image signal state, corresponding to a display characteristic, to a designated image point within a field of view, the image signal state being one of at least two potential signal states, said processor comprising:

means for rendering a current display characteristic state for the designated image point, the means for rendering comprising a first comparator for comparing a current value associated with the designated image point to a first threshold value;

means for summing image point values corresponding to the display characteristic states for a set of image points proximate to the designated image point for a current image frame and for a set of image frames generated in a period of time proximate to the current image frame, to obtain a time and space averaged value for the display characteristic state of the designated image point;

means for comparing the time and space averaged value to at least a second threshold value to render a time and space averaged display characteristic state for the designated image point; and means for calculating a display image signal for the designated image point based at least partially upon the time and space averaged display characteristic state for the designated image point.

32. The image processor space-time filter of claim 31 wherein the display characteristic state designates whether the designated image point will be displayed in color.

33. The image processor space-time filter of claim 32 wherein the color/non-color characteristic for each image point is represented by a single binary bit.

34. The image processor space-time filter of claim 31 wherein the set of image points proximate to the designated image point includes substantially each image point adjacent to the designated image point on the current image frame and the set of image frames generated in a period of time proximate to the current image frame.

35. The image processor space-time filter of claim 31 wherein the set of image points proximate to the designated image point consists of each image point adjacent to the designated image point on the current image frame and the set of image frames generated in a period of time proximate to the current image frame.

36. The image processor space-time filter of claim 31 wherein the set of image frames referenced by the means for summing comprises a set of N temporally adjacent image frames.

37. The image processor space-time filter of claim 36 where N equals about 8 image frames.

38. The image processor space-time filter of claim 31 wherein each image point of each frame used to compute the time and space averaged value for the designated image point is given equal weight by the means for summing.

39. The image processor space-time filter of claim 31 wherein rank order filtering is applied by the means for comparing to assign a signal state based upon a designated range of values associated with particular ranks.

40. The image processor space-time filter of claim wherein the rank order filtering is, in particular, median filtering.

* * * * *